(12) United States Patent
Perez et al.

(10) Patent No.: US 7,553,323 B1
(45) Date of Patent: Jun. 30, 2009

(54) STEERABLE ENDOVASCULAR GRAFT DELIVERY SYSTEM

(76) Inventors: Juan I. Perez, 512 Tower Hill Ave., San Jose, CA (US) 95136; Richard Rapoza, 280 Portola Dr., San Francisco, CA (US) 94131; Mark Lemere, 856 Castro St., San Francisco, CA (US) 94114

( * ) Notice: Subject to any disclaimer, the term of this patent is extended or adjusted under 35 U.S.C. 154(b) by 316 days.

(21) Appl. No.: 10/755,209

(22) Filed: Jan. 8, 2004

(51) Int. Cl.
*A61F 2/06* (2006.01)
(52) U.S. Cl. .................................................... 623/1.11
(58) Field of Classification Search ................ 623/1.23, 623/1.11, 1.13; 606/108, 191–195
See application file for complete search history.

(56) References Cited

U.S. PATENT DOCUMENTS

| | | | |
|---|---|---|---|
| 4,403,985 A | 9/1983 | Boretos | |
| 4,650,466 A | 3/1987 | Luther | |
| 4,723,936 A | 2/1988 | Buchbinder et al. | |
| 4,790,331 A | 12/1988 | Okada et al. | |
| 4,819,634 A | 4/1989 | Shiber | |
| 4,874,371 A | 10/1989 | Comben et al. | |
| 4,917,666 A | 4/1990 | Solar et al. | |
| 4,920,980 A | 5/1990 | Jackowski | |
| 4,921,482 A | 5/1990 | Hammerslag et al. | |
| 4,957,117 A | 9/1990 | Wysham | |
| 4,960,411 A | 10/1990 | Buchbinder | |
| 4,976,689 A | 12/1990 | Buchbinder et al. | |
| 5,037,391 A | 8/1991 | Hammerslag et al. | |
| 5,108,368 A | 4/1992 | Hammerslag et al. | |
| 5,114,403 A | 5/1992 | Clarke et al. | |
| 5,114,414 A | 5/1992 | Buchbinder | |
| 5,123,421 A | 6/1992 | Sinofsky | |
| 5,125,895 A | 6/1992 | Buchbinder et al. | |
| 5,185,004 A | 2/1993 | Lashinski | |
| 5,203,772 A | 4/1993 | Hammerslag et al. | |
| 5,246,420 A | 9/1993 | Kraus et al. | |
| 5,372,587 A | 12/1994 | Hammerslag et al. | |
| 5,378,234 A | 1/1995 | Hammerslag et al. | |
| 5,398,670 A | 3/1995 | Ortiz et al. | |
| 5,431,168 A | 7/1995 | Webster, Jr. | |
| 5,480,382 A | 1/1996 | Hammerslag et al. | |
| 5,578,045 A | 11/1996 | Das | |
| 5,599,305 A | 2/1997 | Hermann et al. | |
| 5,603,697 A | 2/1997 | Grundy et al. | |
| 5,605,543 A * | 2/1997 | Swanson ................ | 604/102.02 |
| 5,624,398 A | 4/1997 | Smith et al. | |
| 5,707,335 A | 1/1998 | Howard et al. | |
| 5,782,828 A | 7/1998 | Chen et al. | |
| 5,817,057 A | 10/1998 | Berenstein et al. | |
| 5,833,656 A | 11/1998 | Smith et al. | |
| 5,843,031 A | 12/1998 | Hermann et al. | |
| 5,860,923 A | 1/1999 | Lenker et al. | |
| 5,860,953 A | 1/1999 | Snoke et al. | |
| 5,876,373 A | 3/1999 | Giba et al. | |
| 5,882,333 A | 3/1999 | Schaer et al. | |
| 5,954,692 A | 9/1999 | Smith et al. | |
| 6,007,531 A | 12/1999 | Snoke et al. | |
| 6,012,034 A | 1/2000 | Hamparian et al. | |
| 6,017,322 A | 1/2000 | Snoke et al. | |

(Continued)

*Primary Examiner*—Alvin J Stewart
(74) *Attorney, Agent, or Firm*—RatnerPrestia (57) ABSTRACT

The present invention embodies delivery systems and methods for delivering medical repair devices that allow the flexibility of the delivery system to be varied and allow the delivery system to be steered and directed in a particular direction.

45 Claims, 9 Drawing Sheets

U.S. PATENT DOCUMENTS

| | | | |
|---|---|---|---|
| 6,027,474 A | 2/2000 | Douk et al. |
| 6,059,738 A | 5/2000 | Stoltze et al. |
| 6,059,767 A | 5/2000 | Noriega |
| 6,066,125 A | 5/2000 | Webster, Jr. |
| 6,071,956 A | 6/2000 | Slepian et al. |
| 6,093,463 A | 7/2000 | Thakrar |
| 6,099,514 A | 8/2000 | Sharkey et al. |
| 6,102,887 A | 8/2000 | Altman |
| 6,126,649 A | 10/2000 | Van Tassel et al. |
| 6,126,654 A | 10/2000 | Giba et al. |
| 6,179,809 B1 | 1/2001 | Khairkhahan et al. |
| 6,190,353 B1 | 2/2001 | Makower et al. |
| 6,198,974 B1 | 3/2001 | Webster, Jr. |
| 6,213,974 B1 | 4/2001 | Smith et al. |
| 6,251,092 B1 | 6/2001 | Qin et al. |
| 6,293,282 B1 | 9/2001 | Lemelson |
| 6,319,227 B1 | 11/2001 | Mansouri-Ruiz |
| 6,338,725 B1 | 1/2002 | Hermann et al. |
| 6,346,099 B1 | 2/2002 | Altman |
| 6,447,521 B1 | 9/2002 | Mouw et al. |
| 6,454,740 B1 | 9/2002 | Mody |
| 6,500,167 B1 | 12/2002 | Webster, Jr. |
| 6,517,477 B1 | 2/2003 | Wendlandt |
| 6,530,913 B1 | 3/2003 | Giba et al. |
| 6,540,725 B1 | 4/2003 | Ponzi |
| 6,551,302 B1 | 4/2003 | Rosinko et al. |
| 6,554,794 B1 | 4/2003 | Mueller et al. |
| 6,575,931 B1 | 6/2003 | Ponzi |
| 6,599,265 B2 | 7/2003 | Bon |
| 6,607,555 B2 | 8/2003 | Patterson et al. |
| 6,623,448 B2 | 9/2003 | Slater |
| 6,623,449 B2 | 9/2003 | Paskar |
| 6,663,613 B1 | 12/2003 | Evans et al. |
| 6,699,179 B2 | 3/2004 | Wendlandt |
| 6,740,104 B1 | 5/2004 | Solar et al. |
| 6,746,446 B1 | 6/2004 | Hill, III et al. |
| 6,758,830 B1 | 7/2004 | Schaer et al. |

* cited by examiner

STEERABLE ENDOVASCULAR GRAFT DELIVERY SYSTEM

BACKGROUND OF THE INVENTION

This invention relates to systems and methods for delivering and deploying endovascular graft components within the vasculature of a patient.

It is well established that various fluid conducting body or corporeal lumens, such as veins and arteries, may deteriorate or suffer trauma so that repair is necessary. For example, various types of aneurysms or other deteriorative diseases may effect the ability of the lumen to conduct fluids and, in turn, may be life threatening. In some cases, the damage to the lumen is repairable only with the use of prosthesis such as an artificial vessel or graft.

An abdominal aortic aneurysm is a sac caused by an abnormal dilation of the wall of the aorta as it passes through the abdomen. The aorta is the main artery of the body, supplying blood to various organs and parts of the body. It arises from the left ventricle of the heart, passes upward, bends over and passes down through the thorax and through the abdomen, and finally divides into the two iliac arteries which supply blood to the pelvis and lower extremities. The aneurysm ordinarily occurs in the portion of the aorta below the kidneys. When left untreated, the aneurysm will eventually cause the sac to rupture with ensuing fatal hemorrhaging in a very short time. The repair of abdominal aortic aneurysms has typically required major abdominal surgery in which the diseased and aneurysmal segment of the aorta is removed and replaced with a prosthetic device, such as a synthetic graft.

For repair of vital lumens such as the aorta, surgical repair is significantly life threatening or subject to significant morbidity. Surgical techniques known in the art involve major surgery in which a graft resembling the natural vessel is spliced into the diseased or obstructed section of the natural vessel. Known procedures include surgically removing the damaged or diseased portion of the vessel and inserting an artificial or donor graft portion inserted and stitched to the ends of the vessel which were created by the removal of the diseased portion. More recently, devices have been developed for treating diseased vasculature through intraluminal repair. Rather than removing the diseased portion of the vasculature, the art has taught bypassing the diseased portion with a prosthesis and implanting the prosthesis within the vasculature. An intra arterial prosthesis of this type has two components: a flexible conduit, the graft, and the expandable framework, the stent (or stents). Such a prosthesis is called an endovascular graft.

As with all major surgeries, there are many disadvantages to the foregoing surgical technique, the foremost of which is the high mortality and morbidity rate associated with surgical intervention of this magnitude. Other disadvantages of conventional surgical repair include the extensive recovery period associated with such surgery; difficulties in suturing the graft to the aorta; the loss of the existing thrombosis to support and reinforce the graft; the unsuitability of the surgery for many patients, particularly older patients exhibiting co-morbid conditions; and the problems associated with performing the surgical procedure on an emergency basis after the aneurysm has already ruptured.

In view of the foregoing disadvantages of conventional surgical repair techniques, techniques have been developed for repairing abdominal aortic aneurysms by intraluminally delivering an aortic graft to the aneurysm site through the use of a catheter based delivery system, and securing the graft within the aorta using an expandable stent. Since the first documented clinical application of this technique, the technique has gained more widespread recognition and is being used more commonly. As vascular surgeons have become more experienced with this endovascular technique, however, certain problems have been encountered.

One of the drawbacks is that rigidity is preferred when maneuvering the delivery system through some portions of vasculature to a repair site while flexibility is preferred when maneuvering the delivery system through other portions of vasculature to a repair site. Furthermore, once the delivery system is at the repair site and the repair device has been deployed, flexibility is preferred when removing the delivery system from the vasculature.

Rigidity facilitates advancing the delivery system through some portions of vasculature by increasing pushability and torquability. Pushability and torquability allow the delivery system to be advanced through areas of the vasculature that are narrowed with a reduced risk that the delivery system may kink or bend. Flexibility facilitates advancing the delivery system through other portion of vasculature, such as tortuous or curved portions, by allowing the delivery system to conform to the vasculature, thereby reducing the risk of damage to the vasculature by the delivery system.

Once the delivery system is at the repair site and the repair device deployed, flexibility facilitates removing the delivery system from within the deployed repair device and retracting the delivery system from the vasculature. Flexibility allows the delivery system to be withdrawn from within the repair device with a reduced risk that the delivery system may get snagged on the repair device and allows the delivery system to conform to the anatomy, thereby reducing the risk of damage to the vasculature as the delivery system is withdrawn.

Another drawback is that precise deployment of a repair device at a repair site may require that the repair device not be deployed at an angle with respect to the vasculature in which it is embedded. A typical repair device for AAA has an anchor frame attached to a graft component, with the anchor frame deployed such that it is embedded in the vasculature at the neck of the aorta. Proper fixation and seal between the repair device and the aorta neck depends upon the anchor frame of the repair device being substantially parallel to the neck when it is deployed. If the anchor frame is deployed at an angle with respect to the neck, a proper seal may not be obtained and leakage may occur.

A rigid delivery system, which may be advantageous for advancement through the vasculature, will not follow the contour of the neck anatomy, thereby making proper deployment of the anchor frame difficult. A flexible delivery system, on the other hand, will conform to the neck anatomy, thereby facilitating deployment of the anchor frame substantially parallel to the neck and a proper seal.

With regard to the method of delivery and deployment of endovascular graft components, there therefore exists a need for a endovascular graft delivery system that allows the flexibility of the delivery system to be varied. Furthermore, there exists a need for a delivery system that facilitates control of the portion of the delivery system containing the repair device such that the anchor frame may be deployed substantially parallel to the wall of the vasculature. The present invention addresses these and other needs.

SUMMARY OF THE INVENTION

Briefly and in general terms, the present invention is embodied in delivery systems and methods for delivering and deploying a medical repair device in vasculature. Specifically, the delivery systems and methods provide variable flexibility and improved control of the delivery systems for precise deployment of a repair device.

Throughout this specification, the term "proximal" shall mean "nearest to the heart," and the term "distal" shall mean "furthest from the heart." Furthermore, the term "inferior" shall mean "nearest the technician", and the term "superior" shall mean "farthest from the technician."

In one aspect of the invention, a system for delivering a medical repair device to a repair site is provided that allows the flexibility of the delivery system to be varied along the entire length of the delivery system. The system has an elongate member on which the repair device is mounted and a jacket or sheath that covers the elongate member and repair device. The repair device is mounted near the superior portion of the elongate member.

The elongate member has a superior portion with a reduced diameter superior tip to facilitate advancing the delivery system through vasculature. Preferably, the superior portion tapers from a constant diameter to the reduced diameter tip. A jacket guard facilitates a smooth transition between the sheath and the reduced diameter tip. The superior portion is relatively flexible. The flexibility of the elongate member may be varied along its length as desired to enable the delivery system to conform to the shape of the vasculature in which it is advanced.

The elongate member provides a guidewire lumen for the delivery system. An inflatable balloon may be provided at the superior end of the inner member with an inflation lumen facilitating inflation and deflation of the balloon via an inlet port at the inferior end. The balloon may be located under the repair device. The repair device may be secured to the superior portion of the inner elongate member by a release wire with a release wire lumen facilitating deployment of the repair device via an inlet port at the inferior end. Preferably, the elongate member has a triple lumen with three inlet ports at the inferior end, the inlet ports providing guidewire access, an inflation lumen, and a release wire lumen.

The repair device may have anchoring mechanisms and hooks to facilitate embedding the device in vasculature. The anchoring mechanisms may be self-expanding or balloon-expandable. It is contemplated that the delivery system may be used with any graft component known in the art.

In one embodiment, the flexibility of the elongate member may be varied using a slidable hypotube disposed within the elongate member. The hypotube is disposed within the guidewire lumen of the elongate member and facilitates advancing the delivery system over a guidewire. A mechanism at the inferior portion of the slidable hypotube allows it to be retracted from or advanced within the elongate member. Because the slidable hypotube extends to the superior portion of the elongate member to the reduced diameter superior tip, retracting the hypotube results in a superior tip that has increased flexibility. The increased flexibility of the superior tip of the elongate member allows it to conform to the vasculature at the repair site, thereby facilitating precise deployment of the repair device anchoring mechanisms.

In another embodiment, the superior portion of the elongate member has a fixed hypotube that is attached to the elongate member. The slidable hypotube is located inside the fixed hypotube. The fixed hypotube provides added rigidity to the superior portion of the delivery system.

In yet another embodiment, the fixed hypotube attached to the elongate member has areas of reduced diameter such that specific lengths along the outside diameter are more flexible. These areas of reduced diameter may be located anywhere along the fixed hypotube where added flexibility is desired. It is contemplated that a fixed hypotube with areas of reduced diameter may be utilized with or without a slidable hypotube located therein.

In another aspect of the invention, a system for delivering a medical repair device to a repair site is provided that allows the superior portion to be bent, thereby facilitating precise deployment of a repair device. The system has an inner member on which the repair device is mounted, an outer member that covers the inner member and repair device and a jacket that covers the inner member, outer member and repair device.

The inner member has a superior portion that is highly flexible. It is contemplated that the aforementioned embodiments of variable flexibility delivery systems may be utilized to achieve the highly flexible superior portion of the inner member.

The inner member has a lumen for a guidewire, preferably, a tri-lumen providing access for a guidewire, a release wire and an inflation lumen. The repair device is mounted near the superior portion of the inner member. Preferably, the repair device has an anchoring mechanism for securing the repair device in the vasculature at the repair site.

The superior portion of the inner member has at least one steering ring coaxially attached thereto. The steering ring is attached to the inner member distal the repair device anchoring mechanism and a plurality of steering wires are attached to eyelets about the circumference of the steering ring. The steering wires act on the steering ring to bend the flexible superior portion of the inner member. By manipulating the steering wires, the superior portion of the inner member may be positioned such that the repair device anchoring mechanism is deployed substantially parallel to the wall of the vasculature at the repair site.

The steering wires extend between the inner member and outer member to a steering mechanism at the inferior portion of the outer member. The steering mechanism facilitates control of the steering wires. When not manipulated by the steering mechanism, the steering ring is held in a "détente" or "normal" position such that the flexible superior portion of the inner member is not bent. It is contemplated that the steering ring may have a convex inferior side and the outer member may have a concave base at the superior end which facilitates the oscillation of the steering ring in response to manipulation by the steering mechanism.

In one embodiment, two steering wires are attached to the steering ring approximately 180° apart. A control knob facilitates control of the steering wires such that the flexible superior portion of the inner member may be bent in either the vertical or horizontal plane.

In another embodiment, four steering wires are attached to the steering ring approximately 90° apart. Two control knobs facilitate control of each steering wire such that the flexible superior portion of the inner member may be bent in both the horizontal and vertical planes.

In yet another embodiment, a plurality of steering rings are provided. The steering wires are attached to the most proximal steering ring and pass through holes in each of the distal steering rings. Manipulating the steering wires causes the steering rings to move in unison such that the flexible superior portion of the inner member bends smoothly along its length.

The steering rings may be located close enough to each other that the convex inferior side of each steering ring operates on the next most distal steering ring, thereby causing the steering rings to move in unison. Alternately, the steering rings may be located apart from each other with small cylindrical steering tubes between adjacent steering rings enclosing the steering wires such that manipulating the most proximal steering ring causes the steering tubes to operate on the distal steering rings, thereby moving all the steering rings in unison.

While it is contemplated that the steering rings and the steering wires may be located distal the distal end of the repair device to prevent the steering rings and steering wires from engaging the graft material of the repair device, the steering rings and steering wires may be located at a more proximal location on the inner member. A flexible cylindrical shield may be used to shield the repair device from the steering rings and steering wires or the outer member may be located inside the distal portion of the repair device between the steering wires and the sheath, thereby allowing the most proximal steering ring to be located adjacent the repair device anchoring mechanism. With the most proximal steering ring located at a more proximal location, better control of the superior portion of the inner member is facilitated.

In yet another aspect of the invention, methods are provided for delivering and deploying a repair device to a repair site using the delivery systems of the present invention. Providing a delivery system with a highly flexible superior portion and a steering mechanism facilitates precise deployment of the repair device.

Other features and advantages of the present invention will become apparent from the following detailed description taken in conjunction with the accompanying drawings, which illustrate, by way of example, the principles of the invention.

DETAILED DESCRIPTION OF THE PREFERRED EMBODIMENTS

The present invention relates to systems and methods for accurately delivering and deploying medical repair devices at a treatment site within a patient's vasculature.

Figure 1:
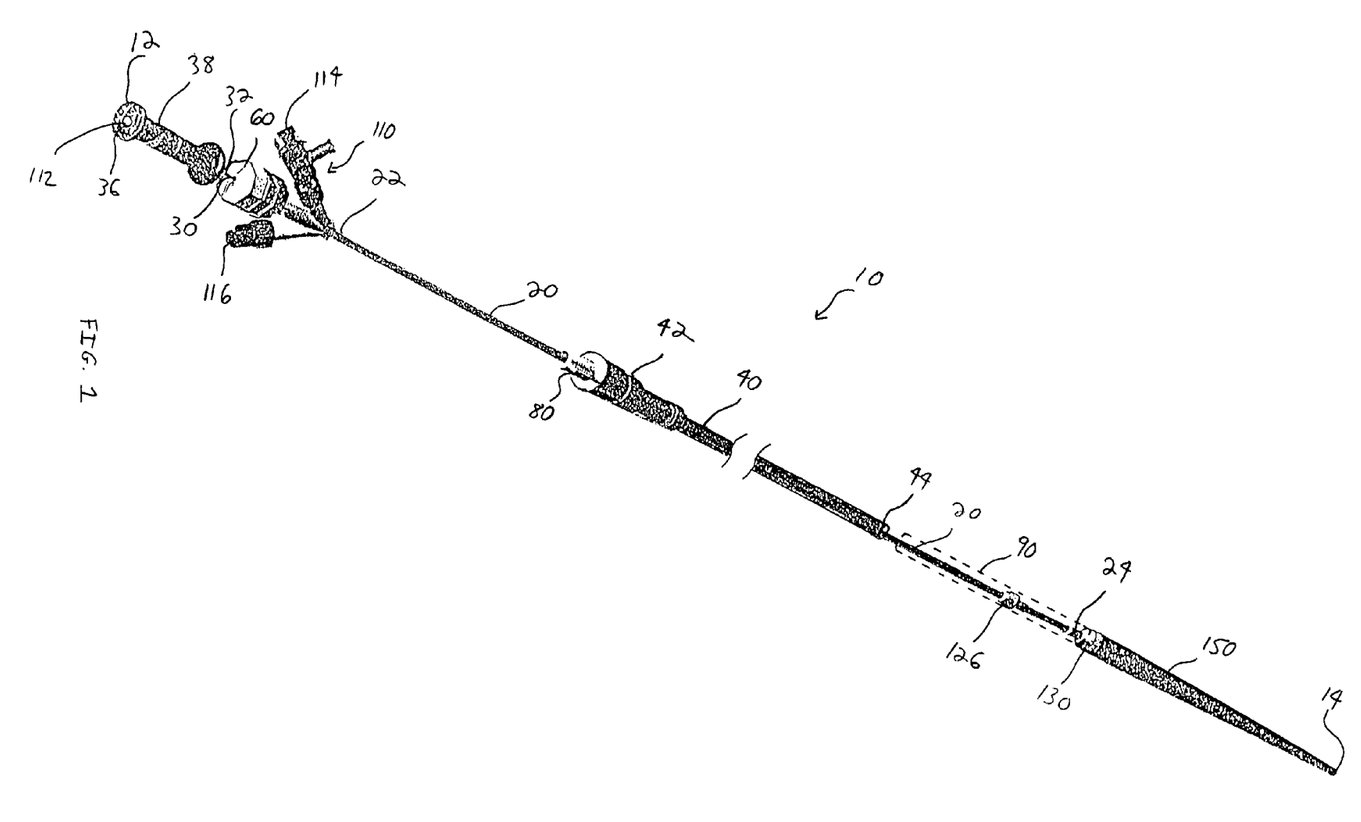
FIG. 1 is a perspective view of a delivery system of the present invention with the sheath assembly retracted and a variable flexibility hypotube advanced within the inner member.

Referring to FIG. 1, an embodiment a main body delivery system 10 of the present invention is shown. The delivery system 10 is defined by an inferior end 12 and a superior end 14 and has three main sections; an inner member 20, a variable flexibility hypotube 30 and a sheath assembly 40.

The elongate inner member 20 is generally tubular and defined by an inferior portion 22 and a superior portion 24. The inner member 20 extends almost the entire length of the delivery system 10 from the inferior end 12 to the superior end 14. The inner member 20 provides the lumen for a guidewire (not shown) over which the delivery system 10 is inserted into a body lumen.

A medical repair device 90, such as an endovascular graft component (indicated by the dotted line in FIG. 1) is releasably secured to the superior portion 24 of the inner member 20. An inflatable balloon (not shown) may be located at the superior portion 24 of the inner member to facilitate expanding the repair device 90 after it has been deployed in the vasculature of a patient.

Figures 2A, 2B, 3:
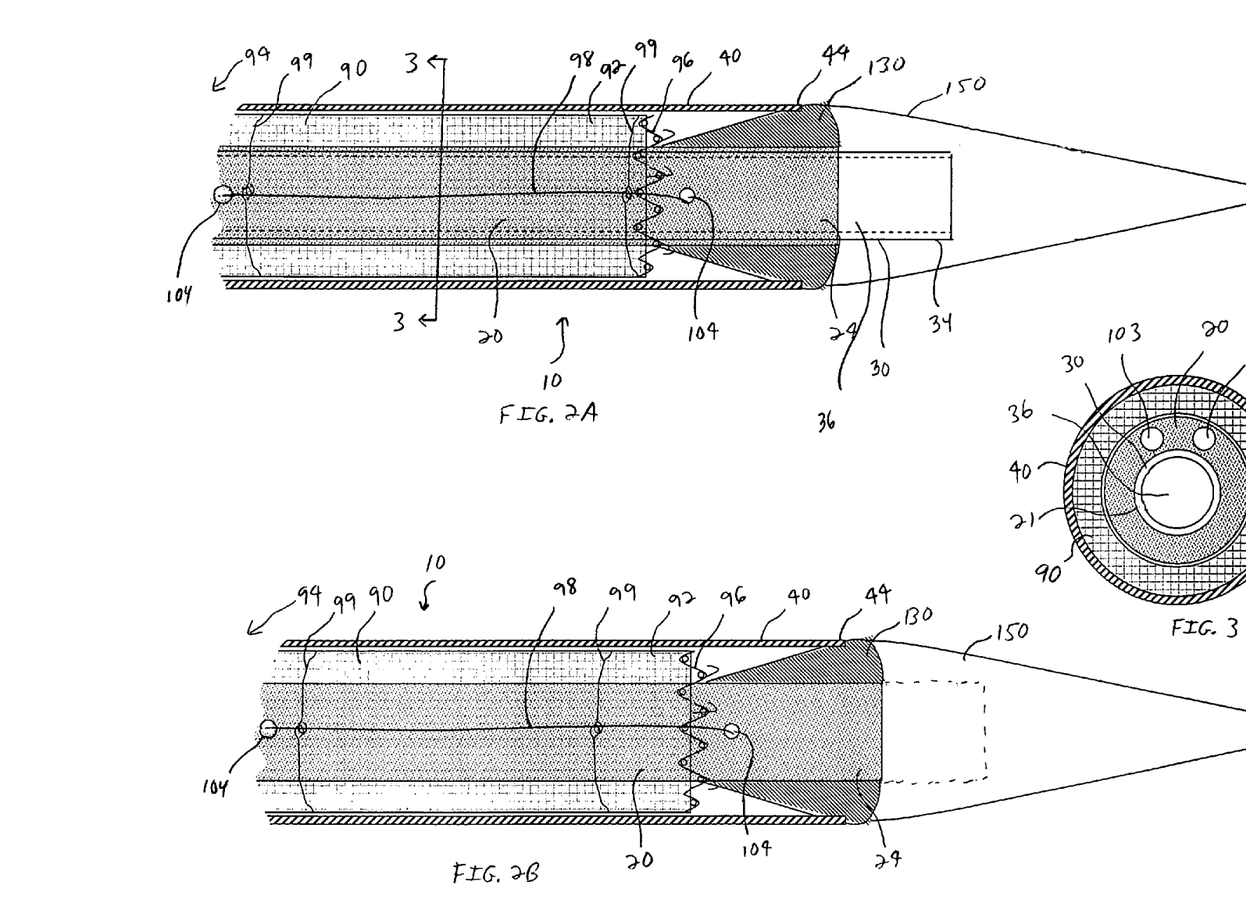
FIG. 2A is a partial cross-sectional view of the superior end of the delivery system of FIG. 1 with the sheath assembly and the variable flexibility hypotube advanced proximally.
FIG. 2B is a partial cross-sectional view of the superior end of the delivery system of FIG. 1 with the sheath assembly advanced proximally and the variable flexibility hypotube retracted distally.
FIG. 3 is a cross-sectional view across line 3-3 of FIG. 2A.

If an inflatable balloon is provided, the inner member 20 will have an inflation lumen 101 therethrough (see FIG. 3). Furthermore, it is contemplated that the repair device 90 may be secured to the inner member 20 utilizing a release wire 98 (see FIGS. 2A and 2B) with a release wire lumen 103 (See FIG. 3) provided through the inner member 20. The inner member 20 preferably is a tri-lumen having a port 110 at the inferior portion 22 with a guidewire inlet 112, inflation inlet 114, and release wire inlet 116 providing exit points for a guidewire (not shown) and the release wire 98 as well as access for inflating and deflating an inflatable balloon (See also FIG. 1).

An aortic frame stop ring 126 is located at the superior portion 24 of the inner member 20 and a jacket guard 130 is located just distal a nose cone 150. The aortic frame stop ring 126 isolates the superior anchor frame 96 at the proximal portion 92 of the repair device 90 (see FIGS. 2A and 2B) from the rest of the repair device. The jacket guard 130 isolates the sheath assembly 40 from the superior anchor frame 96 of the repair device 90. The nose cone 150, having a lumen therethrough with reduced diameter toward the superior end 14, is attached to the superior portion 24 of the inner member 20, the resulting smooth profile of the delivery system 10 facilitating easier maneuverability through a patient's vasculature. The jacket guard 130, nose cone 150 and superior portion 24 of the inner member are made of a material that is highly flexible.

The variable flexibility hypotube 30 is generally tubular and defined by an inferior portion 32 (See FIG. 1) and superior portion 34 (See FIG. 2A). The variable flexibility hypotube 30 is coaxially and slidably disposed within the hypotube lumen 21 (See FIG. 3) of the inner member 20 such the variable flexibility hypotube may slide longitudinally relative to the inner member. The variable flexibility hypotube 30 has a lumen 36 therethrough to facilitate advancing the delivery system 10 over a guidewire (not shown) and a slider mechanism or a grip 38 adapted for controlling movement of the hypotube. A hypotube lock mechanism 60 at the inferior portion 22 of the inner member 20 facilitates releasably locking the variable flexibility hypotube 30 to the inner member, thereby precluding relative movement.

In a preferred embodiment, the delivery system 10 consists of a molded nose cone 150/jacket guard 130/aortic frame stop ring 126 permanently affixed to the superior portion 24 of the inner member which is only a few thousands of an inch thick. The superior portion 34 of the variable flexibility hypotube 30 is inserted through a hole along the longitude of the molded part to the point where the port diameter is reduced. The variable flexibility hypotube 30 is fixed to the inferior portion 22 of the inner member 20 with a grip 38 and lock mechanism 60 allowing for controlled and limited removal of the variable flexibility hypotube The variable flexibility hypotube 30 is shown in its advanced position in FIG. 1. When the variable flexibility hypotube 30 is advanced in the proximal direction, the superior portion 34 extends into the lumen of the nose cone 150 to the location where the diameter is reduced (See FIG. 2A). With the variable flexibility hypotube 30 advanced into the nose cone 150, the superior portion 24 of the inner member has increased rigidity.

When the variable flexibility hypotube 30 is retracted in the distal direction such that the superior portion 34 of the variable flexibility hypotube 30 is distal the distal portion 94 of the repair device 90, the superior portion 24 of the inner member 20 is highly flexible (See FIG. 2B).

The sheath assembly 40 is defined by an inferior end 42 and superior end 44 and is coaxially and slidably disposed over inner member 20 and variable flexibility hypotube 30. A jacket lock mechanism 80 at the inferior end 42 of the sheath assembly 40 facilitates retracting the sheath distally, advancing the sheath proximally and releasably locking the sheath in its retracted or advanced position.

Referring to FIGS. 2A and 2B, the superior end 14 of the delivery system 10 is illustrated. The repair device 90 has a proximal portion 92 and a distal portion 94. A superior anchor frame 96 containing attachment hooks is provided at the proximal portion 92 of the repair device 90 to facilitate imbedding the repair device in a vessel's lumen. The capsule guard 130 isolates the attachment hooks from the sheath assembly 40, thereby preventing the hooks from interfering with retraction of the sheath assembly. A release wire 98 cooperates with a securing mechanism 99, for example suture loops held together by the release wire, to secure the repair device 90 to the inner member 20. One or more securing mechanism are contemplated.

The variable flexibility hypotube 30 is shown in FIG. 2A with the superior portion 34 advanced into the lumen of the nose cone 150. The variable flexibility hypotube 30 adds rigidity to the superior portion 24 of the inner member 20, thereby decreasing the flexibility of the superior end 14 of the delivery system and facilitating advancement through narrow portions of a patient's vasculature.

With reference to FIG. 2B, the variable flexibility hypotube 30 with the superior portion 34 can be retracted to a location distal the distal portion 94 of the repair device. With only the superior portion 24 of the inner member 20 and the guidewire present, the superior end 14 of the delivery system is highly flexible. High flexibility allows the delivery system 10 to be advanced through tortuous or curved portions of a patient's vasculature. Furthermore, once the delivery system is at the repair site, the highly flexible superior portion 24 of the delivery system 10 conforms to the vasculature of the patient and facilitates precise placement of the superior anchor frame 96 of the repair device 90 with respect to the wall of the lumen of the aorta. Furthermore, after the repair device 90 is deployed, high flexibility facilitates withdrawing the delivery system 10 with reduced risk of snagging the graft material or superior anchor frame 96 of the repair device.

Referring to FIG. 3 with continued reference to FIGS. 1 and 2, the tri-lumen of the inner member 20 is illustrated. The hypo-tube lumen 21 extends throughout the length of the inner member 20 and is in fluid communication with the guidewire inlet 112 in the port 110 at the inferior portion 22 of the inner member 20. The hypo-tube lumen 21 facilitates advancing the variable flexibility hypotube 30 through the delivery system 10. The guidewire itself (not shown) can be fed through the guidewire lumen 36. The inflation lumen 101 is in fluid communication with and connects the inflation inlet 114 in the port 110 at the inferior portion 22 of the inner member 20 to an injection orifice (not shown) under an inflatable balloon (not shown), if provided. The inflation lumen 101 facilitates inflating and deflating an inflatable balloon during delivery of the endovascular graft 90. The release wire lumen 103 is in fluid communication with and connects the release wire inlet 116 in the port 110 at the inferior portion 22 of the inner member 20 to release wire orifices 104 near the proximal portion 92 of the repair device 90. The release wire lumen 103 facilitates deploying the repair device 90.

In operation, the delivery system 10 facilitates delivering and precisely deploying the repair device 90 at a repair site within the vasculature of a patient. When increased rigidity of the superior end 14 of the delivery system 10 is desired, such as during advancement through narrow portions of vasculature, the variable flexibility hypotube 30 may be advanced proximally into the superior portion 24 of the inner member 20. When increased flexibility of the superior end 14 of the delivery system 10 is desired, such as during advancement through tortuous or curved portions of vasculature, when precisely positioning the superior anchor frame parallel to the neck of the aorta, or when withdrawing the delivery system from within the deployed repair device 90, the variable flexibility hypotube 30 may be withdrawn distally from the superior portion 24 of inner member 20.

In an alternate embodiment of the delivery system 10, the inner member 20 consists of a molded nose cone 150 with an insert SST tube having a jacket guard 130 and aortic frame stop ring 126. The superior end of a hypotube is permanently fixed to the inferior end of the SST tube. A second variable flexibility hypotube 30 is located inside the fixed hypotube with the superior portion 34 of the variable flexibility hypotube extending into the SST tube to the point where the internal diameter is reduced. The variable flexibility hypotube 30 is attached to a slider mechanism at the inferior portion 22 of the inner member 20 that allows for controlled and limited removal of the variable flexibility hypotube. The fixed hypotube adds rigidity to the delivery system 10 when the variable flexibility hypotube 30 is retracted distally such that the superior portion 34 of the variable flexibility hypotube is no longer inside the superior portion 24 of the inner member 20.

It is contemplated that the delivery system 10 may be utilized both with self-expanding repair devices that use a release wire for deployment and repair devices that are expanded with an inflation balloon. It is further contemplated that a variable flexibility hypotube and or fixed hypotube may be utilized whenever a catheter device with variable flexibility is required.

In another alternate embodiment of the delivery system 10, the fixed hypotube has areas of reduced outside diameter along its length. These areas of reduced outside diameter, for example produced by plunge grinds machined for specific lengths, are more flexible than the rest of the fixed hypotube. Areas of reduced outside diameter may be located anywhere along the length of the fixed hypotube where increased flexibility is desired to match the vasculature at the repair site. It is contemplated that areas of reduced outside diameter on a fixed hypotube may be utilized with or without a variable flexibility hypotube 30 inserted within the fixed hypotube. It is further contemplated that a fixed hypotube with areas of reduced outside diameter may be utilized whenever a catheter device with localized changes in rigidity is required.

Figure 4:
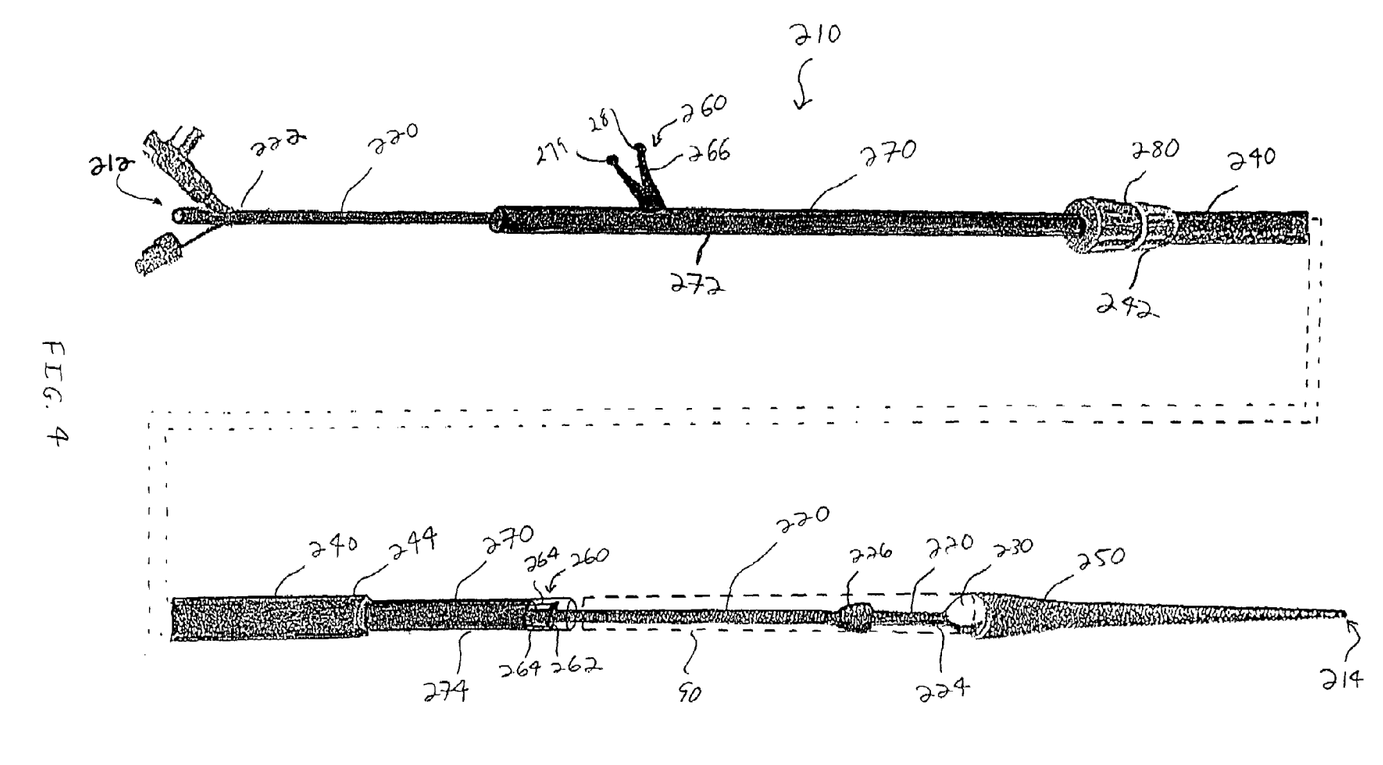
FIG. 4 is a partially fragmented perspective view of an alternate embodiment of a delivery system of the present invention with the sheath retracted and having a steering mechanism.

Referring to FIG. 4, an embodiment an alternate delivery system 210 of the present invention is shown. The delivery system 210 is defined by an inferior end 212 and a superior end 214 and has four main sections; an inner member 220, an outer member 270, a steering mechanism 260 and a sheath assembly 240. The steering mechanism 260 consists of a steering ring 262, steering wires 264 and a control mechanism 266.

The generally tubular elongate inner member 220 is similar to that described previously for the delivery system illustrated in FIG. 1, having an inferior portion 222 and superior portion 224 and a medical repair device 90 releasably secured to the superior portion. An inflatable balloon and release wire may be provided as well as an inflation lumen and release wire lumen. The superior portion 224 of the inner member is highly flexible and it is contemplated that variable flexibility may be achieved utilizing one of the embodiments previously described with regard to the delivery system 10 of FIG. 1. In addition to the aortic frame stop ring 226, jacket guard 230 and nose cone 250 at the superior portion 224 of the inner member 220, a steering ring 262 is fixed to the inner member at a location distal the aortic frame stop ring. It is contemplated that the inner member 220 may have radiopaque markers on the superior portion 224 to facilitate positioning under fluoroscopy.

The steering ring 262 may be attached to the inner member 220 using glue or other adhesives known in the art. It is contemplated that the steering ring 262 may be free-sliding along the inner member 220 with localized increases in diameter on the inner member preventing slippage of the steering ring.

The generally tubular elongate outer member 270 is coaxially disposed over the inner member 220. The outer member 270, having an inferior portion 272 and a superior portion 274, extends from a location near the inferior portion 222 of the inner member 220 to a location near the superior portion 224 of the inner member. Note that the superior portion 274 of the outer member 270 is shown as partially-transparent in order to illustrate the steering ring 262 and steering wires 264.

The sheath assembly 240 is similar to that described previously for the delivery system 10 illustrated in FIG. 1. The sheath assembly 240 has an inferior end 242 and superior end 244 and is coaxially disposed over inner member 220, outer member 270 and a portion of the steering mechanism 260 at the superior portion 224 of the inner member 220. A jacket lock mechanism 280 is located at the inferior end of the sheath assembly 240. The jacket assembly 240 is shown in FIG. 4 in its retracted position, exposing the superior portion 274 of the outer member 270 and the repair device 90 secured to the superior portion 224 of the inner member 220.

The steering mechanism 260 consists of a steering ring 262, steering wires 264 and a control mechanism 266. The steering ring 262 is fixed to the superior portion 224 of the inner member 220 distal the aortic frame stop ring 226 and has eyelets 268 (See FIG. 6) spaced at equidistant locations about its circumference. The steering wires 264 are attached to the eyelets 268 and extend distally between the inner member 220 and outer member 270, exiting the wall of the inferior portion 272 of the outer member distal the inferior end 242 of the jacket assembly 240 where they are attached to the control mechanism 266. Manipulating the steering wires 264 with the control mechanism 266 causes the superior portion 224 of the flexible inner member 220 to bend, thereby allowing the repair device to be positioned properly prior to deployment.

In a configuration having two steering wires 262, control of the superior portion 224 of the flexible inner member 220 in a single plane is possible. In a configuration having four steering wires 262, control in both the horizontal and vertical planes is possible.

Figure 5:
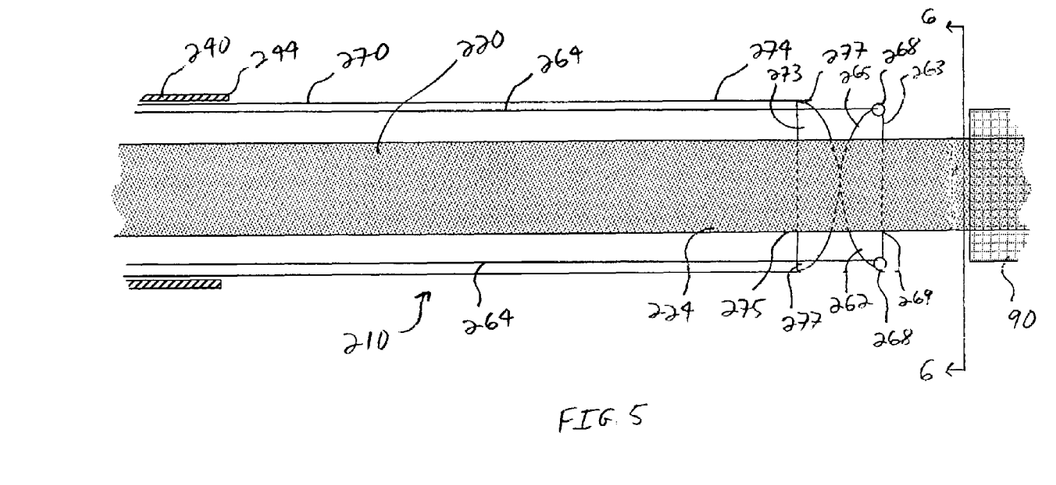
FIG. 5 is a partial cross-sectional view of the superior portion of the outer member of the delivery system of FIG. 4.
Figure 6:
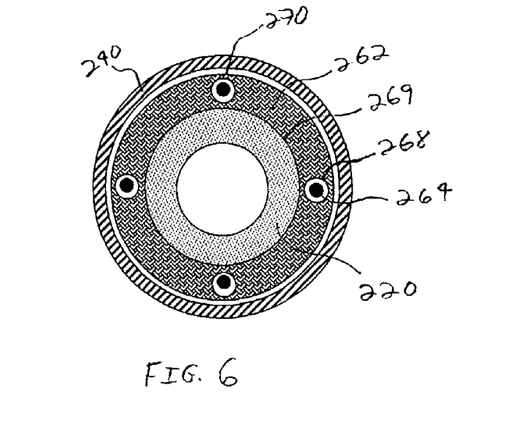
FIG. 6 is a cross-sectional view across line 6-6 of FIG. 5.

Referring to FIGS. 5 and 6, the superior portion 274 of the outer member 270 is illustrated. The steering ring 262 preferably has a flat side 263 facing the proximal direction and a convex side 265 facing the distal direction. An aperture 269 through the center of the steering ring 262 facilitates sliding the steering ring over the inner member 220 and affixing it thereto. The steering wires 264 preferably are made of Nitinol and are 0.012 to 0.020 inches thick. It is contemplated that the outer member 270 may have lumen through which the steering wires 264 extend to the inferior portion 272 of the outer member where they exit to the control mechanism 266.

The superior portion 274 of the outer member 270 may have a concave base 273 with a center aperture 275 to facilitate sliding the inner member 220 therethrough. The concave base 273 abuts the convex side 265 of the steering ring 262, thereby assisting in the oscillation of the steering ring in response to manipulation of the steering wires 264 by the control mechanism 266. The concave base 273 has wire apertures 277 about the circumference to allow the steering wires 264 to pass therethrough.

Figure 7:
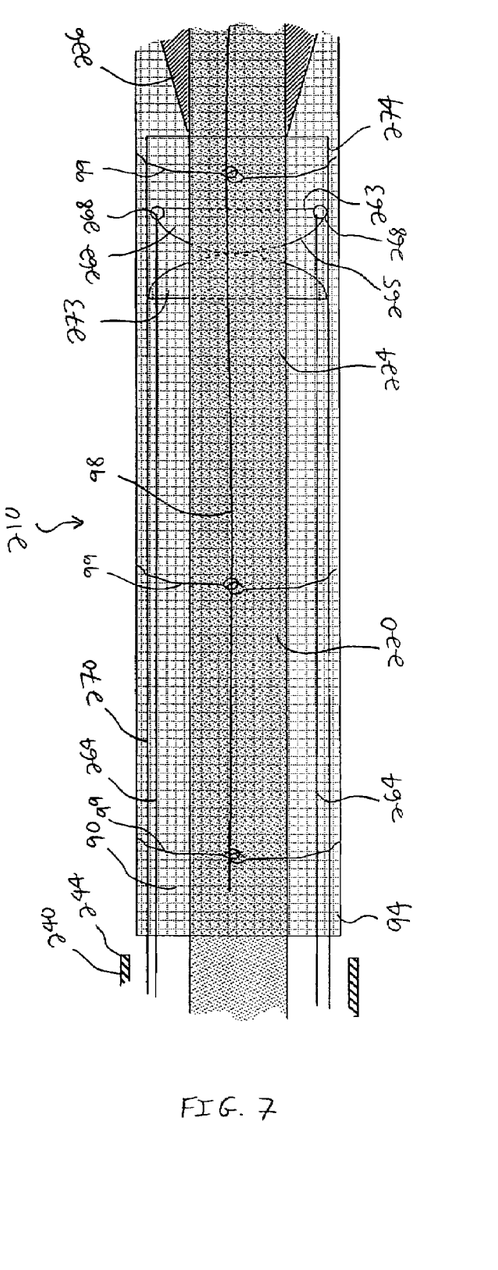
FIG. 7 is a partial cross-sectional view of the superior portion of the outer member of an alternate embodiment of the delivery system of FIG. 4 with the steering ring attached to the inner member near the superior anchor frame of the repair device.

As illustrated in FIG. 7, an alternate embodiment is contemplated with the steering ring 262 attached to the inner member 220 at a point just distal the aortic frame stop ring 226. With the steering ring 262 located at a more superior location on the inner member 220 closer to the superior anchor frame 96 at the superior portion 92 of the repair device 90, better control of the superior portion 224 of the inner member may be achieved, thereby facilitating more precise positioning of the repair device prior to deployment.

In the embodiment illustrated in FIG. 7, the superior portion 274 of the outer member 270 may extend proximally inside the repair device 90, thereby shielding the repair device graft material from the steering ring 262 and steering wires 264 and the graft material may be held between the sheath assembly 240 and the outer member. Alternately, the superior portion 274 of the outer member 270 may extend to a location distal the distal end 94 of the repair device 90, as illustrated in FIG. 5, and a shield (not shown) such as flexible shrink tubing, may be placed between the graft material of the repair device and the steering ring 262 and steering wires 264.

Figure 8:
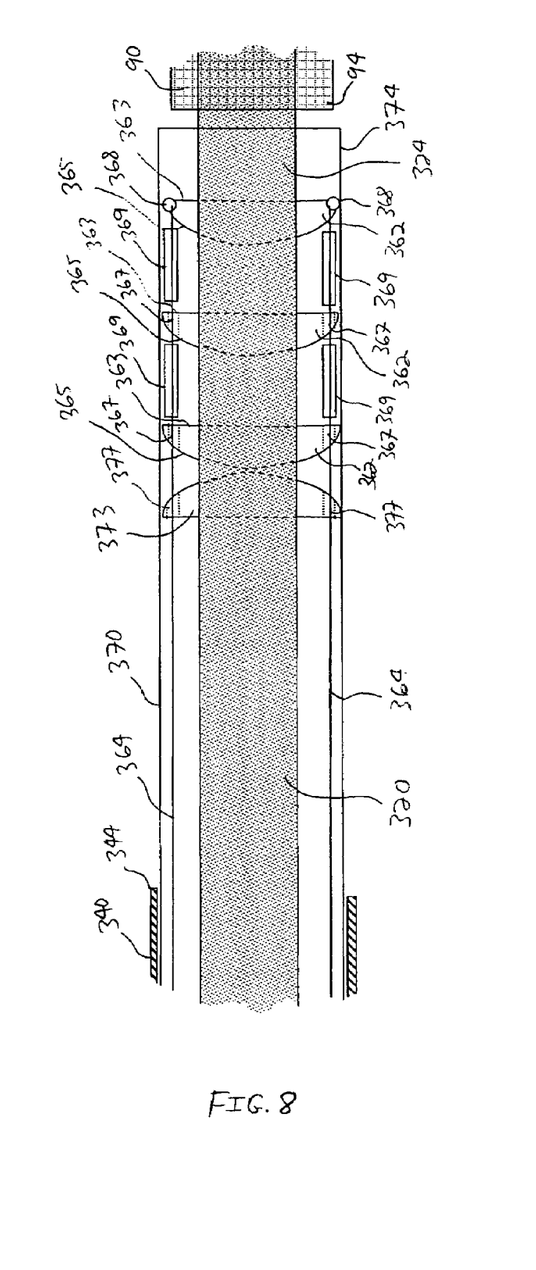
FIG. 8 is a partial cross-sectional view of the superior portion of the outer member of another alternate embodiment of the delivery system of FIG. 4 having multiple steering rings.

In the embodiment illustrated in FIG. 8, multiple steering rings 362 are attached to the superior portion 324 of the inner member 320. The most superior steering ring 362 has eyelets 368 about the circumference to which the steering wires 364 are attached. The distal steering rings 362 have wire apertures 367 about the circumference to allow the steering wires 364 to pass therethrough with the concave base 373 of the outer member 370 abutting the convex side 365 of the most distal steering ring. The additional steering rings 362 facilitate better control and smoother bending of the superior portion 324 of the inner member 320 in response to manipulation of the steering wires 364 by the control mechanism 366 (not shown).

In a typical configuration, pulling the horizontal joystick 281 to the right will cause the flexible portion 224 of the inner member 220 to move to the right and pulling the horizontal joystick to the left will cause the flexible portion of the inner member to move to the left. Similarly, moving the vertical joystick 271 backwards will cause the flexible portion 224 of the inner member 220 to move up and moving the vertical joystick proximally (forward) will cause the flexible portion of the inner member to move down. In this manner, the operator may control the movement of the flexible portion 224 of the inner member 220, and hence the positioning of the wires 364 are attached.

Steering guides 369, for instance small elongate cylindrical tubes, may be located between adjacent steering rings 362 to cause the steering rings to move in unison when the most proximal steering ring is manipulated by the steering wires 364. Alternately, the steering rings 362 may be placed with the convex side 365 of each steering ring abutting the flat side 363 of the next adjacent steering ring such that each steering ring causes the adjacent steering ring to move in unison.

Figure 9:
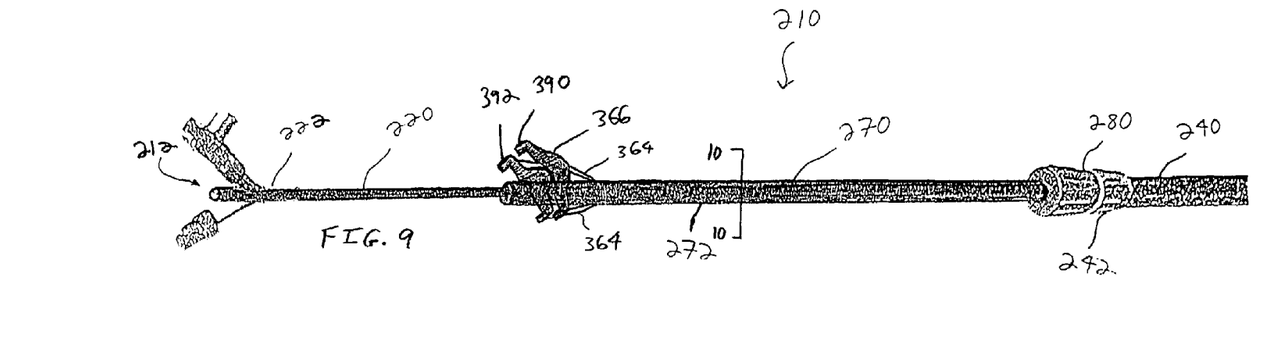
FIG. 9 is a partial perspective view of the inferior portion of the outer member of the delivery system of FIG. 4 illustrating the control mechanism.
Figure 10:
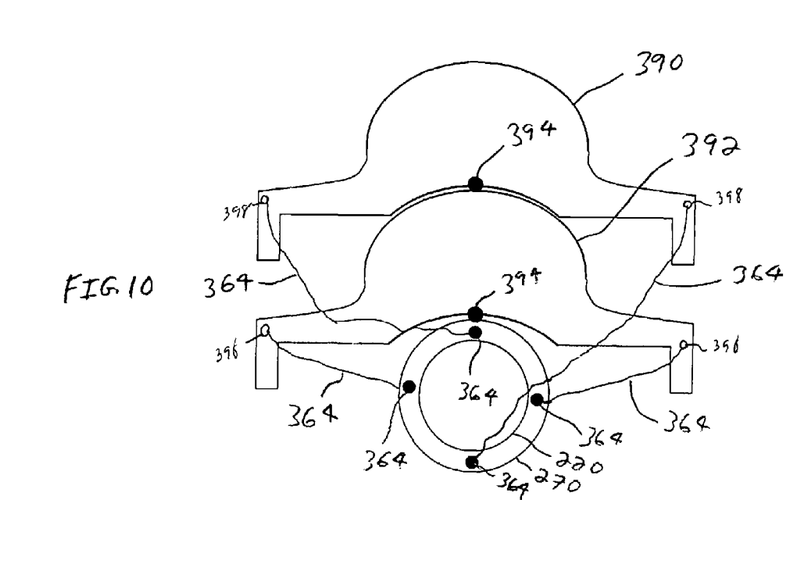
FIG. 10 is a cross-sectional view across line 10-10 of FIG. 9.

Referring to FIGS. 9 and 10, one embodiment of a control mechanism 366 is illustrated. The control mechanism 366 includes a separate vertical controller 390 and horizontal controller 392 that manipulate four steering wires 364 with two steering wires attached to each controller. The controllers 390, 392 each have apertures 398 therethrough to facilitate attaching the steering wires 364. The controllers 390, 392 rotate on pivot points 394 with the horizontal controller 392 rotating on a pivot point on the surface of the outer member 270 and the vertical controller 390 rotating on a pivot point on the horizontal controller. When not acted upon by the operator, a spring mechanism (not shown) maintains the controllers 390, 392 in a "détente" or "normal" position such that the steering wires 364 are not manipulated and the flexible superior portion 224 of the inner member is not bent.

In a typical configuration, rotating distally the right side of the horizontal controller 392 will cause the flexible portion 224 of the inner member 220 to move to the right and rotating distally the left side of the horizontal controller will cause the flexible portion of the inner member to move to the left. Similarly, rotating distally the left side of the vertical controller 390 will cause the flexible portion 224 of the inner member 220 to move down and rotating distally the right side of the vertical controller will cause the flexible portion of the inner member to move up. In this manner, the operator may control the movement of the flexible portion 224 of the inner member 220, and hence the positioning of the repair device 90 superior anchor frame 96, in both the horizontal and vertical planes. Should tension be applied equally to all 4 control wires, the whole catheter would be in compression making it more rigid to increase pushability at desired times during the procedure.

The control mechanisms 266, 366 are illustrated (See FIGS. 4 and 5) as attached to the inferior portion 272 of the outer member 270 and therefore, the inner member 220 and outer member 270 must be fixed together to preclude stretching the steering wires 264, 364. In an alternate embodiment, the control mechanism 266, 366 may be attached to the inferior portion 222 of the inner member 220, thereby enabling the inner member 220 and outer member 270 to move relative to each other.

In a preferred embodiment, the steering ring has four eyelets spaced approximately 90° apart about the circumference to which four steering wires are attached. The concave base of the outer member has four wire apertures. The control mechanism includes two joysticks that receive the steering wires, one joystick facilitating movement of the superior portion of the inner member in the vertical plane and the other joystick facilitating movement of the superior portion of the inner member in the horizontal plane. It is contemplated that the delivery system may be modified to accommodate any number of steering rings and steering wires or any control mechanism known in the art.

It is contemplated that the diameter of the steering rings 262 may be approximately 0.050" to 0.200". It is further contemplated that a delivery system 210 of 18 Fr may be achieved.

Figure 11:
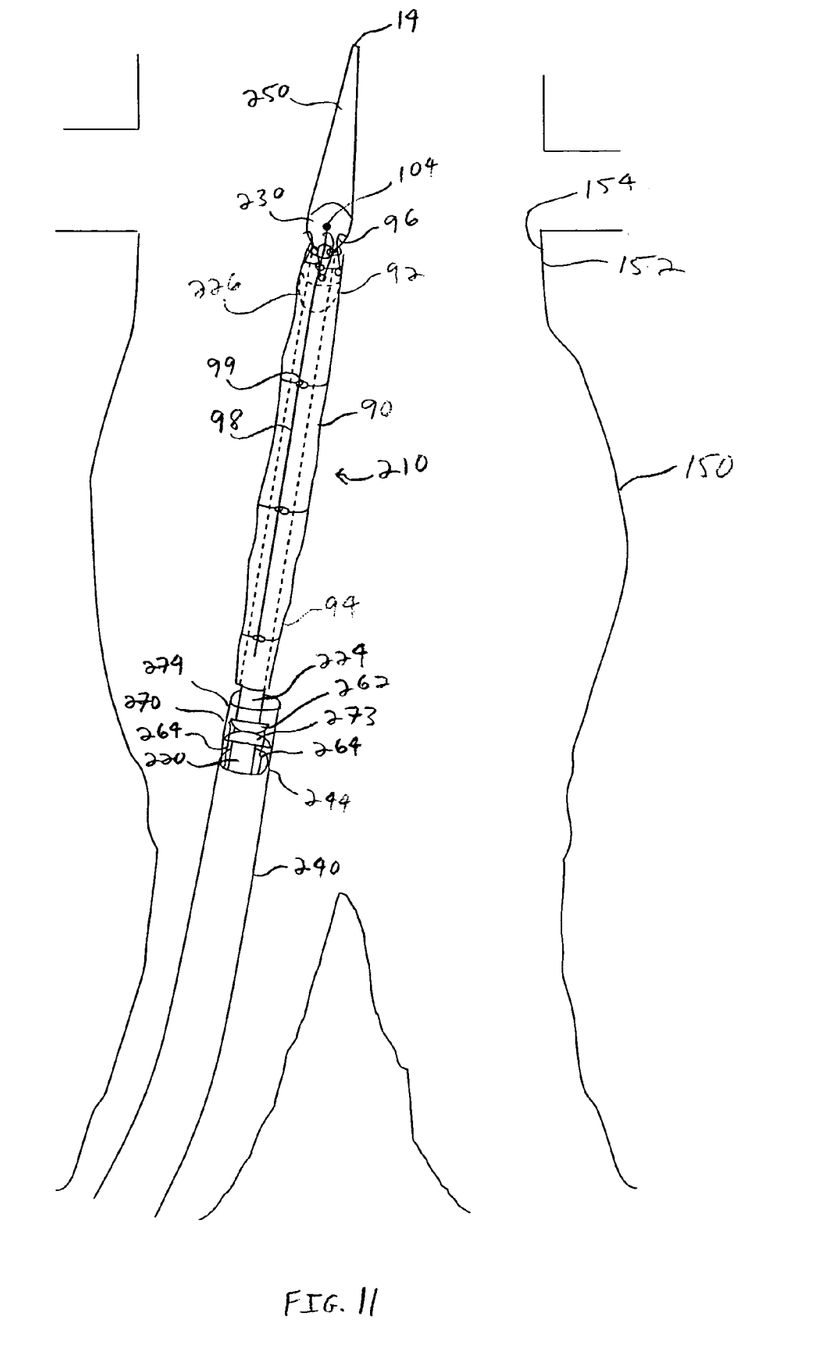
FIG. 11 is a partial perspective view depicting a delivery system of the present invention inserted in the vasculature of a patient with the sheath retracted to expose the repair device.
Figure 12:
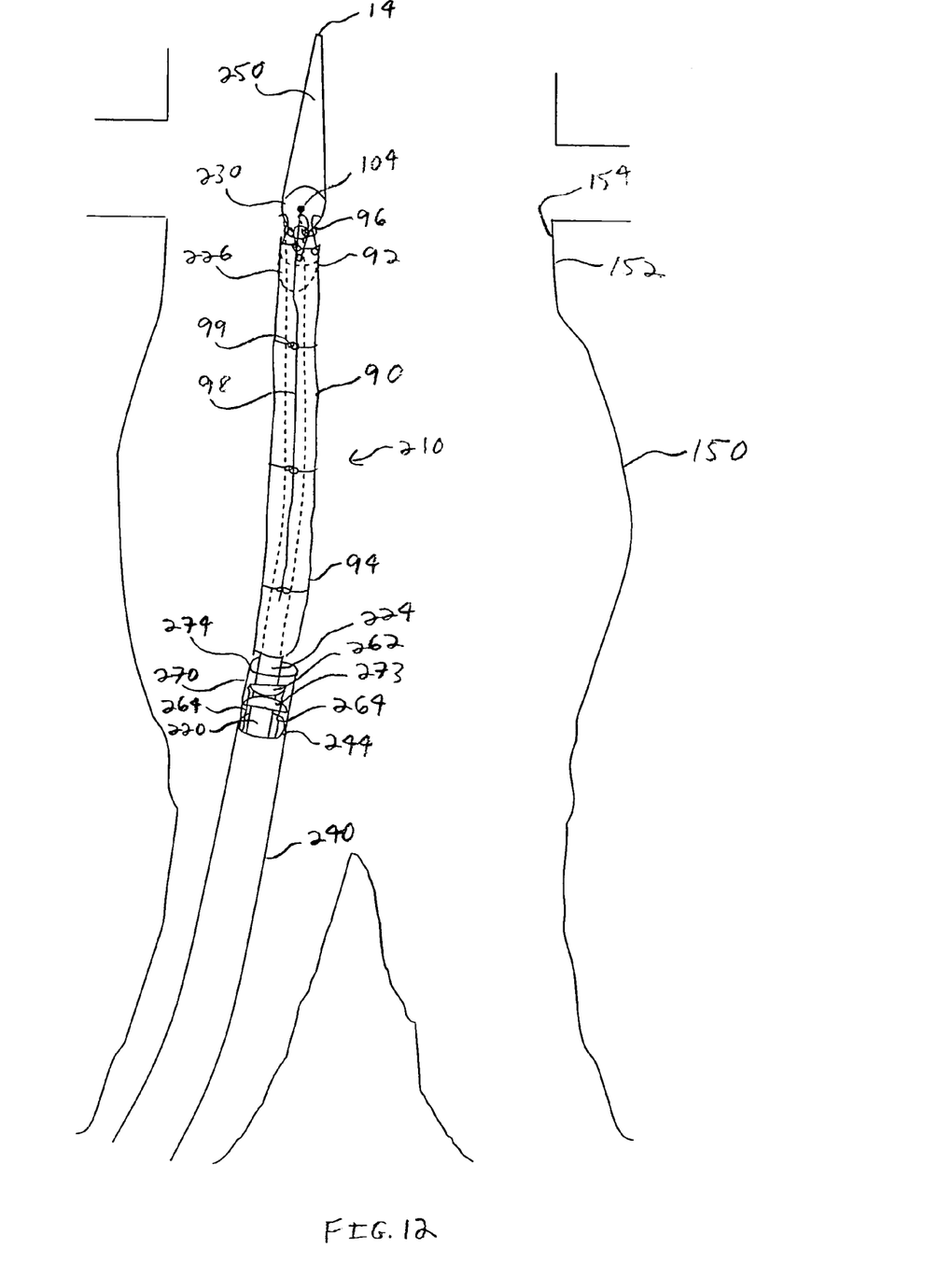
FIG. 12 is a partial cross-sectional view depicting a delivery system of the present invention inserted in the vasculature of a patient with the sheath retracted to expose the repair device and the superior anchor frame positioned substantially parallel to the wall of the aortic neck.
Figure 13:
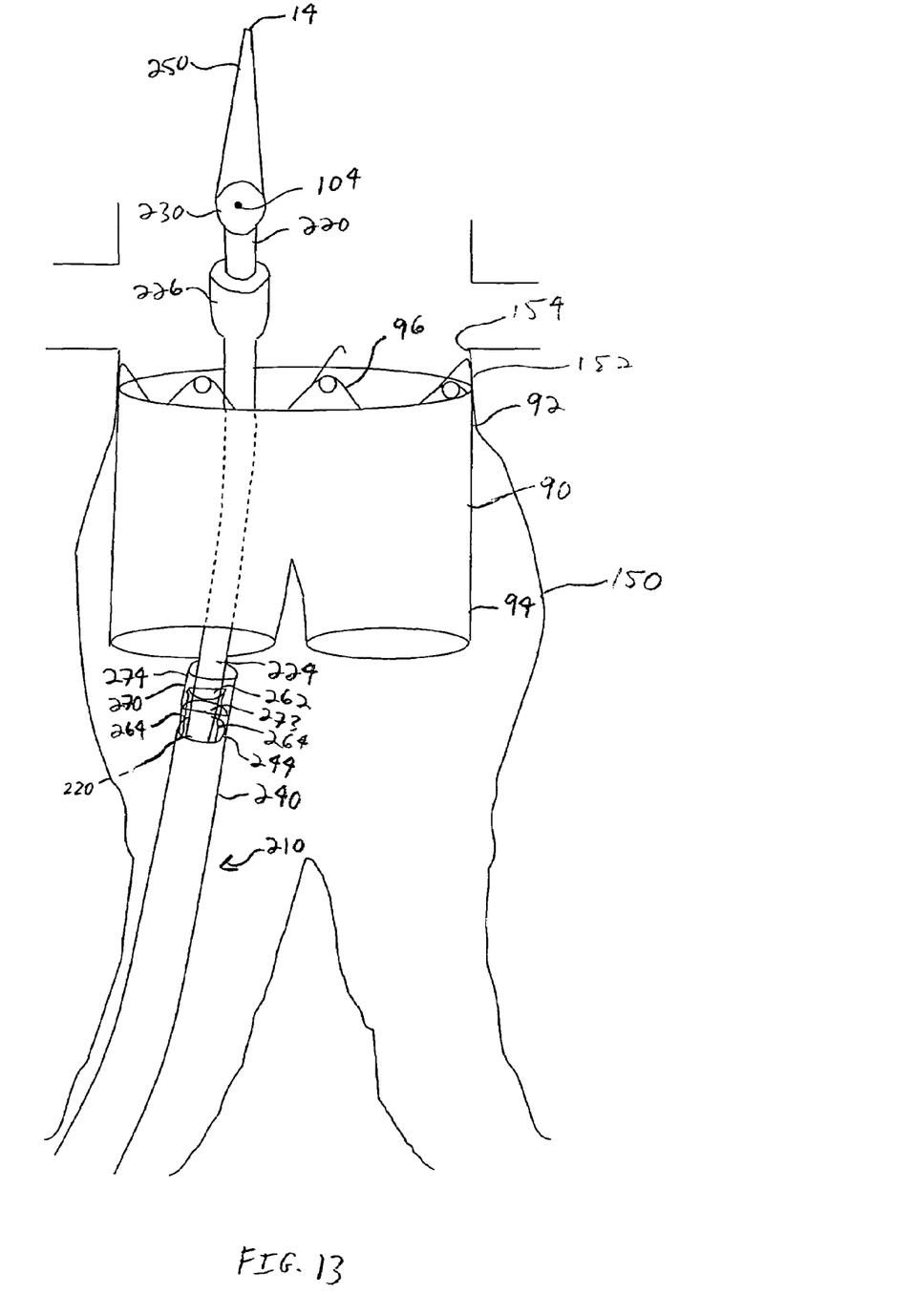
FIG. 13 is a partial cross-sectional view depicting a delivery system of the present invention inserted in the vasculature of a patient with the release wire retracted and a deployed repair device.

Referring to FIGS. 11-13, a method of utilizing the delivery system 210 of the present invention to deploy a repair device 90 is illustrated. The delivery system 210, with the repair device 90 releasably attached to the inner member 220 and the sheath assembly 240 advanced over the outer member 270, inner member and repair device, is advanced through the patient's vasculature to a repair site using methods known in the art. If the delivery system 210 has a variable flexibility hypotube such as that illustrated in FIG. 1, it may be advanced into or retracted from the inner member 220 as desired in order to facilitate advancement of the delivery system through the vasculature.

As illustrated in FIG. 11, the delivery system 210 is advanced such that the superior anchor frame 96 of the repair device 90 is located just proximal the aneurysm 150 with the capsule guard 230 at the neck 152 of the aorta. The sheath assembly 240 is then released via the jacket lock mechanism 280 and retracted until the superior end 244 of the sheath assembly is distal the superior portion 274 of the outer member 270. In this configuration of the delivery system 210, the repair device 90 is exposed but still retained to the inner member 220 by the release wire 98 and securing mechanism 99. The variable flexibility hypotube, if provided, is retracted to increase the flexibility of the superior portion 224 of the inner member 220.

Next, as illustrated in FIG. 12, the control mechanism 266 at the inferior portion 272 of the outer member 270 (not shown) is utilized to manipulate the steering wires 264 which act on the steering ring 262 to cause the flexible superior portion 224 of the inner member 220 to bend. The control mechanism 266 is used to position the superior anchor frame 96 of the repair device 90 substantially parallel to the wall 154 of the vasculature at the neck 152 of the aorta.

With the superior anchor frame 96 of the repair device properly positioned, the repair device is deployed, as illustrated in FIG. 13. The release wire 98 is retracted, releasing the graft securing mechanism 99 and allowing the superior anchor frame 96 to deploy. With the superior anchor frame 96 properly positioned, the hooks will be embedded in the wall 154 of the vasculature and a proper seal will be achieved, thereby precluding leakage of blood into the aneurysm 150.

With the repair device properly deployed, the sheath assembly 240 may be advanced until the superior end 244 of the sheath assembly covers the outer member 270 and inner member 220. The delivery system 210 may then be removed from the patient's vasculature and additional procedures, such as delivery and deployment of additional repair devices, may be performed using methods known in the art.

It is contemplated that the delivery system 210 may be utilized any time it is desired to have a catheter device that can be steered or directed in a particular direction.

It will be apparent from the foregoing that, while particular forms of the invention have been illustrated and described, various modifications can be made without departing from the spirit and scope of the invention. Accordingly, it is not intended that the invention be limited, except as by the appended claims.

What is claimed is:

1. A system for repair of vasculature, comprising:
an elongate member having a superior portion and an inferior portion and at least one lumen therethrough, the superior portion having a superior tip with reduced diameter;
a repair device mounted near the superior portion of the elongate member and having means for anchoring the repair device in vasculature;
a jacket coaxially disposed about the elongate member; and
means for varying the flexibility of the elongate member, the means extending to the superior tip of the elongate member and including structure providing a particular point along the elongate member with alternatively a first flexibility and a second flexibility; and
means for releasably attaching the jacket to the elongate member such that relative movement is precluded.

2. The system of claim 1, wherein the means for varying flexibility comprises a hypotube slidably disposed within the elongate member such that the hypotube may be moved longitudinally relative to the elongate member.

3. The system of claim 2, wherein the slidable hypotube may be advanced into the superior portion of the elongate member such that the hypotube is inside the reduced diameter superior tip.

4. The system of claim 2, the inferior portion of the elongate member further comprising means for limiting the advancement and retraction of the slidable hypotube in the elongate member.

5. The system of claim 2, further comprising means for releasably attaching the slidable hypotube to the elongate member such that relative movement is precluded.

6. The system of claim 1, further comprising a hypotube fixedly attached to the superior portion elongate member.

7. The system of claim 6, wherein the means for varying flexibility comprises areas of the fixed hypotube having reduced outside diameter.

8. The system of claim 1, wherein the repair device is releasably attached to the elongate member by a release wire.

9. The system of claim 1, further comprising an inflatable balloon near the superior portion.

10. The system of claim 9, wherein the inflatable balloon is under the repair device.

11. The system of claim 1, wherein the elongate member comprises a tri-lumen.

12. The system of claim 1, further comprising a stop ring attached to the elongate member adjacent the repair device anchoring means.

13. The system of claim 1, further comprising a jacket guard attached to the elongate member distal the reduced diameter superior tip.

14. The system of claim 1, comprising a molded superior portion permanently affixed to the elongate member, the molded superior portion having a reduced diameter tip, a stop ring adjacent the repair device anchoring means, a jacket guard distal the reduced diameter tip and a tube.

15. A system for repair of vasculature, comprising:
an elongate member having a superior portion and an inferior portion and at least one lumen therethrough, the superior portion having a superior tip with reduced diameter;
a repair device mounted near the superior portion of the elongate member and having means for anchoring the repair device in vasculature;
a jacket coaxially disposed about the elongate member; and
a hypotube slidably disposed within the elongate member, the hypotube extending to the superior tip of the elongate member such that moving the hypotube relative to the elongate member varies the flexibility of the elongate member and provides a particular point along, the elongate member with alternatively a first flexibility and a second flexibility and
wherein the elongate member comprises a second hypotube fixedly attached to the superior portion.

16. A system for repair of vasculature, comprising:
an elongate member having a superior portion and an inferior portion and at least one lumen therethrough, the superior portion comprising a molded tip with an SST tube inserted therein, the SST tube having a superior end with a reduced diameter tip and an inferior portion having a stop ring and jacket guard;
a first hypotube permanently attached to the inferior portion of the SST tube;
a repair device releasably attached near the superior portion of the elongate member by a release wire and having means for anchoring the repair device in vasculature;
a jacket coaxially disposed about the elongate member; and
a second hypotube slidably disposed within the first hypotube, the second hypotube extending into the SST tube reduced diameter tip and attached to a slider mechanism at the inferior portion of the elongate member such that the second hypotube may be moved longitudinally relative to the elongate member.

17. A system for repair of vasculature, comprising:
an inner member having a superior portion and an inferior portion and at least one lumen therethrough, the superior portion of the inner member being highly flexible;
a repair device mounted at the superior portion of the inner member and having means for anchoring the repair device in vasculature;
at least one steering ring coaxially attached at the superior portion of the inner member distal the repair device anchoring means, the at least one steering ring having a center aperture therethrough;
a plurality of steering wires attached to the at least one steering ring such that manipulating the steering wires causes the superior portion of the inner member to bend;
an outer member having a superior portion and an inferior portion and coaxially disposed over at least a portion of the inner member;
means for manipulating the steering wires; and
a jacket coaxially disposed about the inner member- and outer member, the jacket having a superior end and an inferior end.

18. The system of claim 17, wherein the at least one steering ring is attached to the inner member with an adhesive.

19. The system of claim 17, wherein areas of increased diameter on the inner member preclude longitudinal movement of the at least one steering ring.

20. The system of claim 17, the at least one steering ring comprising eyelets about the circumference.

21. The system of claim 17, wherein the steering wires extend distally from the at least one steering ring between the inner member and the outer member.

22. The system of claim 21, the outer member further comprising at least one lumen through which the steering wires extend the at least one lumen exiting the outer member distal the inferior end of the jacket.

23. The system of claim 17, wherein the manipulating means is located on the inferior portion of the outer member.

24. The system of claim 17, wherein the manipulating means is located on the inferior portion of the inner member.

25. The system of claim 24, wherein the outer member can be moved longitudinally relative to the inner member.

26. The system of claim 17, wherein the manipulating means comprises a plurality of steering controllers, each steering controller adapted to manipulate at least two steering wires such that the superior portion of the inner member bends in both the horizontal and vertical planes.

27. The system of claim 17, wherein the manipulating means is adapted to preclude manipulation of the plurality of steering wires in the absence of an external force applied to the steering means.

28. The system of claim 17, wherein the at least one steering ring comprises a flat proximal side and a convex distal side.

29. The system of claim 17, the outer member further comprising a base at the superior portion, the base having a concave proximal side, a center aperture therethrough and a plurality of apertures about the circumference, the concave side abutting the convex side of the at least one steering ring such that the convex side of the at least one steering ring oscillates about the concave side of the base when the steering wires are manipulated.

30. The system of claim 17, wherein the at least one steering ring is located distal the repair device.

31. The system of claim 17, wherein the at least one steering ring is located adjacent the repair device anchoring means.

32. The system of claim 31, wherein the outer member extends longitudinally between the repair device and the at least one steering ring and plurality of steering wires and the superior portion of the outer member is adjacent the repair device anchoring means.

33. The system of claim 31, further comprising a shield between the repair device and the at least one steering ring and plurality of steering wires.

34. The system of claim 33, wherein the shield is formed of flexible shrink tubing.

35. The system of claim 17, comprising a plurality of steering rings.

36. The system of claim 35, wherein the most proximal steering ring has the plurality of steering wires attached thereto and the distal steering rings have apertures about the circumference.

37. The system of claim 35, wherein the plurality of steering rings have a flat proximal side and a convex distal side, the convex side of each steering ring abutting the flat side of the next adjacent steering ring such that the plurality of steering rings move in unison when the steering wires are manipulated.

38. The system of claim 35, further comprising a plurality of steering guides between adjacent steering rings such that the plurality of steering rings move in unison when the steering wires are manipulated.

39. The system of claim 17, wherein the steering wires are formed of Nitinol and are about 0.012 to about 0.020 inches thick.

40. A system for repair of vasculature, comprising:
an inner member having a superior portion and an inferior portion with at least one lumen therethrough, the superior portion of the inner member being highly flexible;
a repair device mounted at the superior portion of the inner member and having means for anchoring the repair device in vasculature;
a plurality of steering rings coaxially attached to the inner member distal the repair device anchoring means, the most proximal steering ring having a plurality of steering wires attached thereto;
means for causing the plurality of steering rings to bend in unison when the steering wires are manipulated such that manipulating the steering wires causes the superior portion of the inner member to bend in both the horizontal and vertical planes;
an outer member coaxially disposed over at least a portion of the inner member; means for manipulating the steering wires; and
a jacket coaxially disposed about the inner member and outer member.

41. A system for repair of vasculature, comprising:
an inner member having a superior portion and an inferior portion with at least one lumen therethrough, the superior portion having a superior tip with reduced diameter;
a repair device mounted at the superior portion of the inner member and having means for anchoring the repair device in vasculature;
means for varying the flexibility of the inner member, the means extending to the reduced diameter superior tip of the inner member;
at least one steering ring coaxially attached to the inner member distal the repair device anchoring means and having a plurality of steering wires attached thereto such that manipulating the steering wires causes the superior portion of the inner member to bend;
an outer member coaxially disposed over at least a portion of the inner member; means for manipulating the steering wires; and
a jacket coaxially disposed about the inner member and outer member.

42. The system of claim 41, wherein the means for varying flexibility comprises a hypotube slidably disposed within the inner member such that the hypotube may be moved longitudinally relative to the inner member.

43. The system of claim 41, further comprising a hypotube fixedly attached to the superior portion of the inner member and wherein the means for varying flexibility comprises areas of the hypotube having reduced outside diameter.

44. A method of repairing vasculature, comprising:
providing a catheter having an inner member coaxially disposed within an outer member, the superior portion of the inner member being highly flexible and having a repair device mounted thereon, the repair device having means for anchoring in vasculature, at least one steering ring coaxially attached to the inner member, the at least one steering ring having a plurality of steering wires attached thereto, and means for manipulating the steering wires such that manipulating the steering wires causes the superior portion of the inner member to bend;
advancing the catheter in vasculature such that the anchoring means of the repair device is adjacent a repair site;
manipulating the steering wires to position the anchoring means of the repair device; deploying the anchoring means of the repair device.

45. The method of claim 44, the inner member having the means for varying the flexibility of the inner member disposed therein and comprising retracting the variable flexibility means such that the inner member is highly flexible.

* * * * *